United States Patent
Thomas et al.

(10) Patent No.: US 8,513,604 B2
(45) Date of Patent: Aug. 20, 2013

(54) DETECTION DEVICE AND PARTICLE BEAM DEVICE HAVING A DETECTION DEVICE

(75) Inventors: Christian Thomas, Ellwangen (DE); Lucian Stefan, Ulm (DE)

(73) Assignee: Carl Zeiss Microscopy GmbH, Oberkochen (DE)

( * ) Notice: Subject to any disclaimer, the term of this patent is extended or adjusted under 35 U.S.C. 154(b) by 209 days.

(21) Appl. No.: 12/925,704

(22) Filed: Oct. 27, 2010

(65) Prior Publication Data

US 2011/0220793 A1 Sep. 15, 2011

(30) Foreign Application Priority Data

Oct. 30, 2009 (DE) .................. 10 2009 046 211

(51) Int. Cl.
*G01J 1/00* (2006.01)

(52) U.S. Cl.
USPC ...................................... 250/336.1

(58) Field of Classification Search
USPC ..................... 250/336.1, 307, 310
See application file for complete search history.

(56) References Cited

U.S. PATENT DOCUMENTS

| | | |
|---|---|---|
| 4,117,323 A | 9/1978 | Greer et al. |
| 6,498,345 B1 | 12/2002 | Weimer et al. |
| 7,317,515 B2 | 1/2008 | Buijsse et al. |
| 7,425,701 B2 | 9/2008 | Steigerwald et al. |
| 2003/0053048 A1 | 3/2003 | Bennett et al. |
| 2003/0127609 A1* | 7/2003 | El-Hage et al. ............ 250/574 |
| 2004/0090621 A1* | 5/2004 | Bennett et al. ............ 356/300 |

FOREIGN PATENT DOCUMENTS

| | | |
|---|---|---|
| DE | 197 31 226 A1 | 8/1998 |
| DE | 198 28 476 A1 | 12/1999 |
| DE | 103 01 579 A1 | 7/2004 |
| EP | 0 914 669 B1 | 4/2004 |
| EP | 2 194 565 A1 | 6/2010 |
| GB | 1 369 314 | 10/1974 |

OTHER PUBLICATIONS

P.T.E. Roberts, et al., "A CCD-Based Image Recording System for the CTEM," Ultramicroscopy 8, 1982, pp. 385-396.

(Continued)

*Primary Examiner* — David Porta
*Assistant Examiner* — Faye Boosalis
(74) *Attorney, Agent, or Firm* — Muirhead and Saturnelli, LLC

(57) ABSTRACT

A detection device and a particle beam device having a detection device ensure a good efficiency in detecting interaction particles and electromagnetic radiation. The detection device has a detector for detecting electromagnetic radiation and/or interaction particles and a filter element through which the electromagnetic radiation is transmitted. The filter element prevents the interaction particles from striking the detector such that the filter element is situated to move between a first position and a second position, the filter element in the first position being situated in relation to the detector in such a way that the filter element prevents the interaction particles from striking the detector. The filter element in the second position is situated in relation to the detector in such a way that the filter element allows the interaction particles to strike the detector. As an alternative, the filter element may be an object holder.

22 Claims, 6 Drawing Sheets

(56) References Cited

OTHER PUBLICATIONS

T. Barfels, et al., "Kathodolumineszenz an Quarz, Quarzglas und dünnen amorphen Siliciumdioxidschichten [Cathodoluminescence of Quartz, Silica and Thin Amorphous SiO2 Layers]," Wuppertal 1998, 1 p. (with English Machine translation) (published in Materials Research Society Symposium, Spring Meeting 1999, Proceedings vol. 560).

B. J. Luff, et al., "Cathodoluminescence of synthetic quartz," J. Phys.: Condens. Matter 2, 1990, pp. 8089-8097.

Schott AG, "LITHOSIL® Synthetisches Quarzglas," <http://www.schott.com/advanced_optics/german/our_products/lithography/fused_silica.html>, visited 2009, 2 pp. (with English brochure entitled "LITHOSIL Synthetic Fused Silica," Advanced Optics, 9 pp.).

* cited by examiner

DETECTION DEVICE AND PARTICLE BEAM DEVICE HAVING A DETECTION DEVICE

TECHNICAL FIELD

This application relates to a detection device and a particle beam device having a detection device. In particular this application relates to a scanning electron microscope or a transmission electron microscope, which is designed to have a detection device. The detection device according to the system described herein and the particle beam device according to the system described herein may be used in particular to examine transparent objects, in particular biological objects. The biological objects may include, in particular, biological thin sections and biological samples labeled by immunolabeling or quantum dots.

BACKGROUND OF THE INVENTION

Electron beam devices, in particular a scanning electron microscope (hereinafter also referred to SEM) and/or a transmission electron microscope (hereinafter also referred to as TEM) are used for examining objects (samples) to obtain information about the properties and behavior of these objects under certain conditions.

In the case of an SEM, an electron beam (hereinafter also referred to as a primary electron beam) is generated by a beam generator and focused by a beam guidance system on an object to be examined. The primary electron beam is guided in a grid pattern by a deflecting device over a surface of the object to be examined. The electrons of the primary electron beam then interact with the material of the object to be examined. As a result of this interaction, in particular electrons are emitted from the surface of the object to be examined (so-called secondary electrons) and electrons of the primary electron beam are backscattered (so-called backscattered electrons). The secondary electrons and backscattered electrons are detected and used for image generation. This yields an image of the surface of the object to be examined.

In the case of a TEM, a primary electron beam is also generated by a beam generator and focused by a beam guidance system on an object to be examined. The primary electron beam passes through the object to be examined. As the primary electron beam passes through the object to be examined, the electrons of the primary electron beam interact with the material of the object to be examined. The electrons passing through the object to be examined are imaged by a system including an objective lens and a projective lens on a luminescent screen or on a detector (for example, a camera). In addition, it is also possible to provide for detecting electrons backscattered on the object to be examined and/or secondary electrons emitted by the object to be examined by another detector to image an object to be examined. The imaging is performed in the scanning mode of a TEM. Such a TEM is usually referred to as a STEM.

The electrons passing through the object in a TEM are detected by a detector connected downstream from the object—starting from the beam generator toward the object along the optical axis of the TEM.

In a SEM, the secondary electrons or backscattered electrons are detected with a detector, for example, which is situated inside the objective lens or in an area between the objective lens and the beam generator. For example, a SEM having the features mentioned above is known, in which a first detector and a second detector are offset from one another along the optical axis of the SEM for detecting the secondary electrons and backscattered electrons. Both the first detector and the second detector have an aperture. The first detector situated in the vicinity of the object to be examined is used to detect the electrons which emerge from the object to be examined at a relatively large solid angle whereas the second detector which is situated in the area of the beam generator is used to detect the electrons emerging from the object to be examined at a relatively small solid angle. To arrive at the second detector, these electrons pass through the aperture of the first detector which is provided for the passage of the primary electron beam.

Furthermore, an SEM which also has the aforementioned features is also known from the prior art. This known SEM is also additionally provided with a first detector and with a second detector. The first detector and the second detector are offset from one another along an optical axis of the SEM. The first detector is provided with an adjustable aperture to mask out secondary electrons so they do not strike the first detector.

With regard to the prior art cited above, reference is made, for example, to DE 198 28 476 A1 and DE 103 01 579 A1, which are incorporated herein by reference.

A particle beam, for example an electron beam, guided onto an object, may also interact with the object (in addition to the interaction particles already mentioned above) in such a way that electromagnetic radiation occurs in the form of cathodoluminescence. By detecting and analyzing the cathodoluminescence (for example, by an intensity analysis and spectral analysis), properties of the material of the object may be determined, for example, the determination of recombination centers, lattice defects, impurities and phase formations. The preceding list is to be understood merely as an example and is not conclusive.

Electron beam devices using which cathodoluminescence is also analyzed are known from the prior art. For example, there is a known electron beam device using which an object situated in a sample chamber is bombarded with an electron beam. Due to an interaction of the electron beam with the material of the object, the object emits light due to cathodoluminescence (hereinafter also referred to as cathodoluminescent light). The cathodoluminescent light is guided to a detector by an ellipsoidal mirror through a window situated in a wall of the sample chamber. The detector is thus situated outside of the sample chamber. In the case of another known electron beam device, using which cathodoluminescence is also analyzed, an object situated in a sample chamber is also bombarded with an electron beam. The object emits cathodoluminescent light, which is guided via a waveguide out of the sample chamber and further to a detector.

In the known prior art, the cathodoluminescent light is therefore detected at a relatively great distance from the object emitting the cathodoluminescent light. This results in an inferior efficiency in detecting the cathodoluminescent light because the cathodoluminescent light is detected only in a very restricted solid angle with respect to the object. Thus a portion of the photons of the cathodoluminescent light is not detected by the detector. Furthermore, the path from the source of the emitted cathodoluminescent light (i.e., the object) to the detector is relatively long. Intensity losses occur due to this path alone, which has a negative effect on the signal detected by the detector overall. Furthermore, intensity losses also occur in the waveguides used. In the known prior art, multiple waveguide elements linked together are also used, so intensity losses may also occur at a coupling point between two different waveguide elements.

Using waveguides and the ellipsoidal mirror also has another disadvantage. Because of the waveguides or the ellipsoidal mirror used, a portion of the secondary electrons or backscattered electrons is obscured, so that they are no longer able to strike a detector. This results in poor imaging.

Another disadvantage of the known electron beam devices in which the cathodoluminescent light is analyzed is that each detector used in these electron beam devices is essentially designed to detect only interaction particles or to detect only electromagnetic radiation. Therefore, in the case of the known electron beam devices, multiple detectors are always provided to be able to detect both interaction particles and electromagnetic radiation. This results in a greater complexity with regard to construction and assembly of these electron beam devices because vacuum feed-throughs and control units must be provided for each detector.

With regard to the prior art cited above, reference is made to DE 197 31 226 A1, EP 0 914 669 B1 and GB 1 369 314, which are incorporated herein by reference.

Accordingly, it would be desirable to provide a detection device and a particle beam device having a detection device, using which good efficiency in detecting interaction particles and electromagnetic radiation is ensured.

SUMMARY OF THE INVENTION

According to the system described herein, a detection device includes at least one detector for detecting electromagnetic radiation and/or interaction particles. For example, when a particle beam strikes an object, interaction particles occur due to interactions of the particle beam with the object (more specifically, with the material of the object). For example, the interaction particles are the backscattered electrons already mentioned above and/or the secondary electrons, but also transmission electrons. The object may thus also be designed to be so thin that interaction particles are transmitted through the object. The electromagnetic radiation may be, for example, luminescence, such as cathodoluminescence or fluorescence, which occurs due to irradiation of an object with the help of a particle beam or a light source. The detection device according to the system described herein may also have at least one filter element, which is transparent to the electromagnetic radiation. In other words, the filter element may be designed in such a way that electromagnetic radiation is transmitted through the filter element. The filter element may be situated movably between a first position and a second position. In the first position, the filter element may be situated in relation to the detector in such a way that the filter element prevents the interaction particles from striking the detector. In the second position, the filter element may be situated in relation to the detector in such a way that the filter element allows the interaction particles to strike the detector.

The detection device according to the system described herein has the advantage that the detector for detecting the electromagnetic radiation may not be situated outside of a sample chamber of a particle beam device but instead may be situated inside the sample chamber. For this reason, the use of waveguides and vacuum bushings may be omitted in a particle beam device in which the detection device is used, for example, so that the losses of intensity described above do not occur in comparison with the prior art. The efficiency of the detection device according to the system described herein is increased in comparison with that of the prior art in this way.

Furthermore, the detection device according to the system described herein allows both interaction particles and electromagnetic radiation to be detected by using only a single detector. It is thus not required to provide an additional detector for detecting interaction particles or electromagnetic radiation. In the case of the system described herein, this is ensured by the fact that the movably designed filter element may be movable between a first position and a second position. In the first position, the filter element may be situated between an object to be examined and the detector in such a way that the filter element prevents the interaction particles from striking the detector. The interaction particles are practically filtered out. For example, they are decelerated in the filter element or are backscattered by the filter element. In the second position, however, the filter element may no longer be situated between an object and the detector, so that the filter element allows the interaction particles to strike the detector.

The detection device according to the system described herein also allows accurate differentiation of whether a detection signal detected by the detector has occurred because of interaction particles or because of electromagnetic radiation. It is possible to separate a first detection signal, generated by the electromagnetic radiation, from a second detection signal, generated by interaction particles. In this way the first detection signal generated by the detector in a measurement in which the filter element is in the first position (i.e., in the position in which only electromagnetic radiation strikes the detector) is subtracted from a second detection signal in a measurement in which the filter element is in the second position (i.e., in the position in which interaction particles and electromagnetic radiation strike the detector). This yields an unambiguous determination of a signal which is based essentially only on the interaction particles. This may be used for imaging.

Due to the system comprising the detector and the filter element described here, the system described herein makes it possible to situate the detector and the filter element very close to an object, for example, at a distance of approximately 5 mm to approximately 30 mm from the object. In particular it is also provided that an object which is to be examined and is situated on a movably designed object holder, may be situated relatively close to the filter element, for example, at a distance of 0.2 mm to 3 mm therefrom. However, the system described herein is not limited to the aforementioned range. Instead it is also possible in particular to situate an object to be examined directly on the filter element, as will be discussed in greater detail below. Due to the aforementioned systems, it is possible for the detector of the detection device according to the system described herein to cover a relatively large solid angle. This is understood in particular to mean that the detector is capable of detecting a relatively large portion of the interaction particles originating from an object and of the electromagnetic radiation. For example, both the filter element and the detector may be designed to be much larger than an object, so it is possible for the detector to essentially completely cover the half-space directed toward the object to be examined. This is the half-space into which the electromagnetic radiation is emitted by an object or into which the interaction particles arrive from an object. In comparison with a detector according to the prior art situated outside of the sample chamber, the detector of the detection device according to the system described herein is able to detect a greater number of photons of the electromagnetic radiation and/or a greater number of interaction particles. The efficiency of the detector is therefore increased in comparison with the prior art.

The detection device may further have one of the aforementioned features or combinations of features as further explained in greater detail below. Again in the case of this detection device, at least one detector is provided for detecting electromagnetic radiation. The electromagnetic radiation may be, for example, luminescence, such as cathodoluminescence or fluorescence, which occurs due to irradiation of an object with a particle beam or a light source. When an object is irradiated by a particle beam, interaction particles are generated when the particle beam strikes the object due to interactions of the particle beam with the object (more specifically, with the material of the object). For example, the interaction particles may be not only the above-mentioned backscattered electrons and/or secondary electrons but also transmission electrons. Furthermore, the detection device according to the system described herein may have at least one filter element designed in such a way that electromagnetic radiation is transmitted through the filter element and interaction particles are not transmitted through the filter element. Furthermore, it is provided that the filter element may be designed as an object holder. The filter element may be designed as a microscope slide, for example. This allows an object that is to be examined to be situated very close to the detector. This in turn results in an increased efficiency of the detector. Reference is made to the preceding discussion with regard to additional advantages.

In another embodiment of the detection device according to the system described herein, it is additionally or alternatively provided that the filter element may be made of a nonluminescent material. A nonluminescent material as mentioned above and below is understood to refer to a material in which no luminescence at all or only a low luminescence occurs, such that the intensity of the low luminescence is not superimposed on and does not influence the electromagnetic radiation emitted by an object, in particular in interaction with a particle beam or in interaction with the light of a light source. Whether an influence is to be expected due to the low luminescence depends in particular on the object to be examined. If the intensity of the electromagnetic radiation emitted by the object is much greater than the intensity of the low luminescence of the filter element, then an influence is probably not to be expected. An influence is probably also not to be expected if the low luminescence of the filter element occurs in a wavelength range, which is completely different from the wavelength range of the electromagnetic radiation emitted by the object. A measurement performed using the detector is thus not interfered with and the measurement results achieved are not subject to a great error. Therefore, this ensures that the electromagnetic radiation or at least the essential portion of the electromagnetic radiation emitted by the object to be examined is detected by the detector.

In an embodiment of the system described herein, the filter element may be made of silicon dioxide, for example. It has been found in experiments that silicon dioxide (also known as quartz glass) is surprisingly nonluminescent, according to the definition given above, at room temperature (approximately 23° C.) or in a range of ±5° C. deviating slightly from room temperature (i.e., approximately 18° C. to 28° C.). When a particle beam in the form of an electron beam strikes a semiconductor, electrons are lifted from the valence band into the conduction band, resulting in the formation of electron-hole pairs. As soon as an electron and a hole recombine, a photon is emitted and detected. The preceding also readily applies to direct semiconductors (for example, GaAs). For indirect semiconductors (for example, silicon), the preceding is not readily applicable. The greater the purity of the indirect semiconductor, the lower is the intensity of the emitted electromagnetic radiation when an electron beam strikes the indirect semiconductor. Furthermore, defect centers in the indirect semiconductor are filled with electrons due to the electron beam supplied. They are then no longer actively luminescent. Furthermore, the luminescence induced by an electron beam in a very pure silicon dioxide is a function of temperature. A fundamental luminescence is detectable essentially at temperatures below 220° K (i.e., below −53.15° C.). For example, synthetic quartz glass from the company Schott, distributed under the brand name LITHOSIL Q1, is a suitable nonluminescent material. This material may be characterized by a high homogeneity and absence from inclusions and bubbles.

In contrast with the aforementioned, it has been found in experiments that a variety of optically transparent materials used in the field of optics, for example, calcium fluoride ($CaF_2$) or sapphire ($Al_2O_3$), are luminescent and therefore may be unsuitable for the system described herein.

Alternatively or in addition to this, the filter element may be designed as an opposing field grating. By applying a suitable voltage, it is possible to deflect interaction particles in such a way that they do not strike the detector.

In yet another embodiment of the detection device according to the system described herein, it is additionally or alternatively provided that the detection device may have a reflective unit, which is situated movably. The reflective unit may be movable between at least one reflection position and at least one resting position. In the reflection position, the reflective unit reflects a portion of the electromagnetic radiation toward the detector. This embodiment is suitable in particular for examining an object which is transparent to electromagnetic radiation. For example, the object may be transparent to electromagnetic radiation of the same wavelength range as the electromagnetic radiation emitted by the object. The electromagnetic radiation emitted by the object not toward the detector but rather in another direction, for example, in the direction opposite the detector, is reflected by the reflective unit onto the detector, so that the electromagnetic radiation is also transmitted through the object, for example, and then strikes the detector. Thus, for example, it is possible to detect not only the electromagnetic radiation emitted into a first half-space directed toward the detector, but also to detect the electromagnetic radiation emitted into a second half-space opposite the first half-space. Detection of the electromagnetic radiation over the entire solid angle ($4\pi$ detection) is thus fundamentally possible in this way. In an embodiment, the reflective unit is designed as a self-contained element, for example, a hemisphere, which, however, has a first aperture for admission of a particle beam. Furthermore, the reflective unit may be provided with a second aperture, through which the filter element is guided as it moves from the first position into the second position (and vice-versa).

In another embodiment of the detection device according to the system described herein, it is additionally or alternatively provided that the detector may have at least one first detector segment and at least one second detector segment. The first detector segment may be used to detect interaction particles and electromagnetic radiation striking the detector at a first angle of incidence. However, the second detector segment may be used for detecting interaction particles and electromagnetic radiation striking the detector at a second angle of incidence. It is thus possible to draw conclusions about the dependence of the interaction particles and the electromagnetic radiation on the angle of incidence. These detector segments may be of any shape and configuration. For example, they may be designed as circular segments or ring segments and may detect the interaction particles or the electromagnetic radiation in the corresponding solid angle.

In another embodiment of the detection device according to the system described herein, it is additionally or alternatively provided that the detection device may have a moving device for moving the filter element. The moving device may be designed in such a way that the filter element is movable back and forth between the first position and the second position. For example, the aforementioned movements take place in an interval in the range of 100 ms to 2 s. It is possible in this way to perform in particular time-resolved measurements for a preselected location on an object to be examined.

In another embodiment of the detection device according to the system described herein, it is additionally or alternatively provided that the detector may be designed as a semiconductor detector. For example, the detector may be designed as a photodiode, in particular as an avalanche photodiode. Although it was already mentioned above, reference is made explicitly here to the fact that the detector is designed for detecting cathodoluminescence in particular. Again alternatively or additionally thereto, the detector may also be designed as a STEM detector.

According further to the system described herein, a particle beam device includes a detection device, which may have at least one of the aforementioned features or a combination of at least two of the aforementioned features. The particle beam device according to the system described herein thus has the same advantages as those mentioned further above. The particle beam device according to the system described herein may have a sample chamber. An object to be examined using the particle beam device is placed in the sample chamber. Furthermore, the particle beam device may have a beam generator, which generates a particle beam, for example, an electron beam. The particle beam is focused on the object using an objective lens mounted on the particle beam device. When the particle beam strikes the object, interaction particles and electromagnetic radiation are generated due to interactions of the particle beam with the object (more specifically, with the material of the object). For example, the interaction particles are not only the backscattered electrons and/or the secondary electrons already mentioned above, but also transmission electrons. Thus the object may also be designed to be so thin that interaction particles are transmitted through the object. The electromagnetic radiation may be, for example, cathodoluminescence. The electromagnetic radiation may additionally or alternatively also be generated by irradiation of the object to be examined using another light source. As mentioned above, the particle beam device according to the system described herein is provided with the detection device according to the system described herein. The detector of the detection device may be provided in the sample chamber. In addition to this, for example, it is also provided that the filter element, the reflective unit and/or the moving device may also be situated in the sample chamber.

In another embodiment of the particle beam device according to the system described herein, the detector may be used to detect the electromagnetic radiation and the interaction particles. In addition, the filter element which is transparent to the electromagnetic radiation may be provided. In other words the filter element may be designed in such a way that the electromagnetic radiation is transmitted through the filter element. The filter element may be situated movably between the first position and the second position. In the first position, the filter element may be situated in relation to the detector, so that the filter element prevents the interaction particles from striking the detector. In the second position, the filter element may be situated in relation to the detector in such a way that the filter element allows the interaction particles to strike the detector.

In an alternative embodiment of the particle beam device according to the system described herein, it is provided that the detector may be used to detect the electromagnetic radiation. In addition, the filter element may be designed in such a way that the electromagnetic radiation is transmitted through the filter element and the interaction particles are not transmitted through the filter element. Furthermore, it is provided that the filter element may be designed as an object holder. For example, the filter element may be designed as a microscope slide. This makes it possible to place the detector and the object to be examined in close proximity to one another. This in turn results in an increased efficiency of the detector. With regard to the additional advantages, reference is made to the preceding discussion.

In yet another embodiment of the particle beam device according to the system described herein, it is additionally or alternatively provided that the particle beam device may have an optical axis and that—starting from the beam generator—the object may be situated first along the optical axis and then the detector. In the first position, in which the filter element prevents the interaction particles from striking the detector, the filter element may be situated between the detector and the object on the optical axis. This embodiment is suitable in particular for examining very thin objects because in this way either the electromagnetic radiation emitted by the thin object or the particles transmitted through the thin object are detected. For example, objects having a thickness from a few nm to several µm, for example, 10 nm to 5 µm, are examined.

According further to the system described herein, a method is provided for using a particle beam device or a detection device having one of the aforementioned features or having one of the aforementioned combinations of features for examining a transparent object, in particular a biological object. For example, the particle beam device according to the system described herein may be suitable in particular for examining biological thin sections and/or biological samples, for example labeled by fluorescence markers, immunolabeling or quantum dots. The luminescence of the object in this examination, for example, in the form of cathodoluminescence or fluorescence, may be detected in a predefinable solid angle, for example, in a solid angle of $4\pi$.

According further to the system described herein, another particle beam device, which may have at least one of the aforementioned features or combination of features and is explained in greater detail below. The particle beam device may again have a sample chamber. An object which is examined using the particle beam device may be placed in the sample chamber. Furthermore, the particle beam device may have a beam generator, which generates a particle beam, for example, an electron beam. The particle beam may be focused on the object using an objective lens mounted on the particle beam device. When the particle beam strikes the object, interaction particles and electromagnetic radiation occur due to interactions of the particle beam with the object. For example, the interaction particles may be the backscattered electrons, the secondary electrons and/or the transmission electrons already mentioned above. The electromagnetic radiation may be cathodoluminescence, for example. Furthermore, at least one detector, which is situated in the sample chamber, may be provided on the particle beam device. The detector may be used for detecting the interaction particles. In addition, the particle beam device may have at least one filter element, which is transparent to the interaction particles. In other words, the filter element may be designed in such a way that the interaction particles are transmitted through the filter element. The filter element is situated to move between a first position and a second position. In the first position, the filter element may be positioned in relation to the detector, in such a way that the filter element prevents the electromagnetic radiation from striking the detector. In the second position, the filter element may be situated relative to the detector, in such a way that the filter element allows the electromagnetic radiation to strike the detector. The aforementioned additional particle beam device according to the system described herein has the same advantages as those already mentioned above, with the difference that the filter element in the additional particle beam device according to the system described herein may be used for filtering the electromagnetic radiation. For example, an aluminum foil having a foil thickness in the range of 10 nm to 20 nm, for example, is suitable as the filter element.

BRIEF DESCRIPTION OF THE DRAWINGS

Embodiments of the system described herein are explained in greater detail below on the basis of the figures, which are briefly described as follows.

DETAILED DESCRIPTION OF VARIOUS EMBODIMENTS

Figure 1:
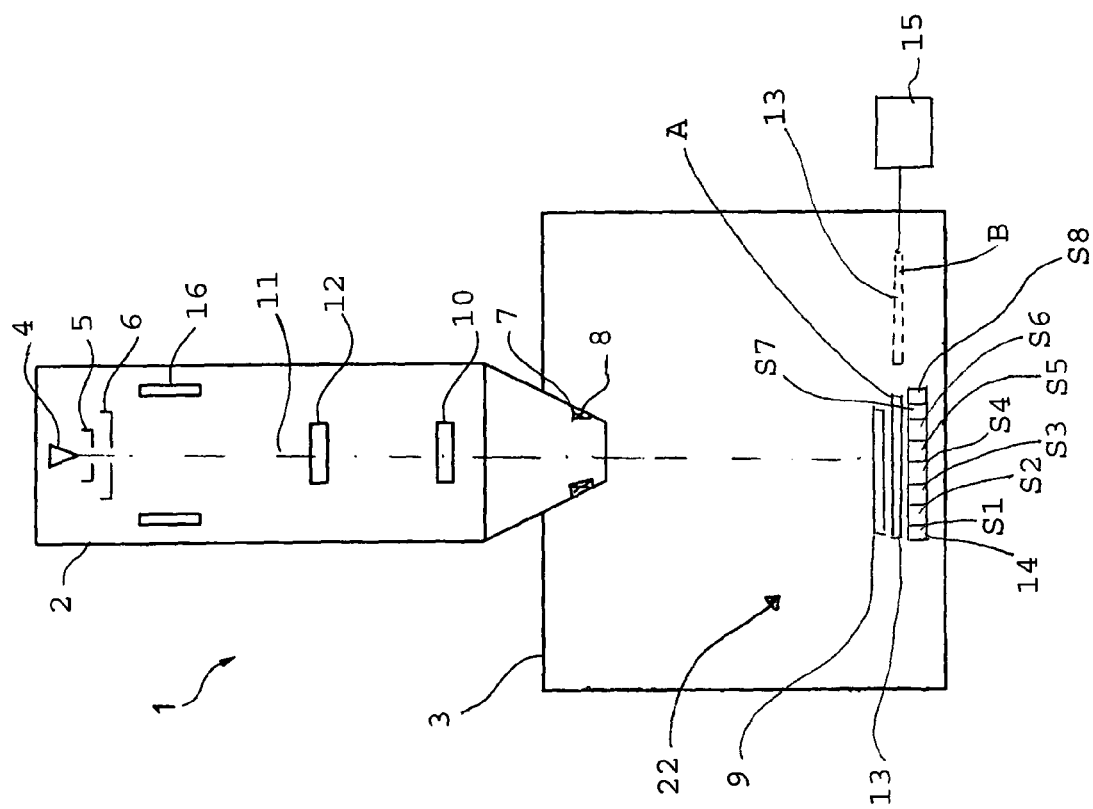
FIG. 1 shows a schematic view of a first exemplary embodiment of a particle beam device according to the system described herein.

FIG. 1 shows a schematic view of a first exemplary embodiment of a particle beam device 1 according to the system described herein. Particle beam device 1 has a particle beam column 2, which is situated on a sample chamber 3. Particle beam column 2 is designed as an electron beam column.

Particle beam column 2 has a beam generator 4 in the form of an electron source (cathode) and a system, which includes a first electrode 5 and a second electrode 6. Second electrode 6 forms one end of a beam guidance tube (not shown). For example, beam generator 4 is designed as a thermal field emitter. Electrons exiting from beam generator 4 are accelerated to a preselectable potential because of a potential difference between beam generator 4 and second electrode 6 (for example, to an energy in the range of 1 keV to 300 keV) and form a primary electron beam which is guided by a beam guidance system 16. The beam guidance tube is guided through an aperture of a magnetic lens acting as an objective lens 7. Objective lens 7 is provided with pole shoes (not shown) in which coils (not shown) are situated. Furthermore, a scanning device 8 is provided, by which the primary electron beam is deflected and may be scanned over an object 9 placed in the sample chamber 3.

Secondary electrons and/or backscattered electrons generated due to the interaction of the primary electron beam with object 9 are detected by a first detector system of particle beam device 1 for the imaging. For this purpose, a first detector 10 is provided at the object end along optical axis 11 of particle beam column 2, while a second detector 12 is provided at the source end along optical axis 11 (i.e., toward beam generator 4). Furthermore, first detector 10 and second detector 12 are offset from one another. As already explained above, the aforementioned first detector system, including first detector 10 and second detector 12, is optional, but may be desirably used in connection with an embodiment of the system described herein.

A second detector system is provided with particle beam device 1. Thus, starting from beam generator 4 as seen toward object 9, first object 9, then a filter element 13 and finally a third detector 14 are positioned along optical axis 11. Filter element 13 and third detector 14 are part of a detection device 22 according to the system described herein, which is provided in particle beam device 1.

Third detector 14 has the following function. When the primary electron beam strikes object 9, not only are the secondary electrons and backscattered electrons mentioned above generated due to the interactions of the primary electron beam with object 9, but also electromagnetic radiation occurs in the form of cathodoluminescent light. If object 9 is designed to be thin enough, then some electrons of the primary electron beam will also pass through object 9 (transmission electrons). Third detector 14 is then used only for detecting the electromagnetic radiation and the transmission electrons.

In an alternative embodiment (not shown), electromagnetic radiation may be generated by excitation of object 9 by a light source.

Filter element 13 having a thickness of approximately 0.5 mm is transparent to the electromagnetic radiation (for example, in a wavelength range of 185 nm to 2.5 μm). In other words, filter element 13 is designed in such a way that electromagnetic radiation is transmitted through filter element 13. However, filter element 13 is not transparent to the transmission electrons. Filter element 13 is situated movably between a first position A and a second position B. For this purpose, a moving device 15 which is part of detection device 22 and is situated outside of sample chamber 3 is provided. Moving device 15 is connected to filter element 13. It is capable of moving filter element 13 from a first position A into a second position B (and vice-versa). Filter element 13 is shown in dotted lines in second position B.

In first position A, filter element 13 is situated between object 9 and third detector 14. In this position, filter element 13 prevents the transmission electrons from striking third detector 14. Thus only electromagnetic radiation strikes third detector 14 and is detected by it. In second position B, filter element 13 is no longer situated between object 9 and third detector 14. In this position, both the electromagnetic radiation and the transmission electrons now strike third detector 14. To obtain a detection signal based essentially only on the transmission electrons, a first detection signal, which has been ascertained by third detector 14 in first position A and is based on the detected electromagnetic radiation, is subtracted from a second detection signal which was ascertained using third detector 14 in second position B and which is a summation signal based on the electromagnetic radiation and the transmission electrons. This yields a detection signal corrected for the electromagnetic radiation and based fundamentally only on the transmission electrons.

Filter element 13 is made of a nonluminescent material, reference being made here to the definition given above in this regard. In the exemplary embodiment presented here, very pure silicon dioxide, which is distributed under the brand name LITHOSIL Q1 by Schott, is used as the material. This material has proven to be particularly nonluminescent. This makes it possible for only the electromagnetic radiation emitted by object 9 to be detected by third detector 14. The measurement results thus achieved are therefore not subject to any great errors.

Third detector 14 is segmented and has a plurality of detector segments, namely a first detector segment S1, a second detector segment S2, a third detector segment S3, a fourth detector segment S4, a fifth detector segment S5, a sixth detector segment S6, a seventh detector segment S7 and an eighth detector segment S8. Aforementioned detector segments S1 through S8 are used to detect the transmission electrons and the electromagnetic radiation striking third detector 14 at various angles of incidence. These detector segments may be formed as circular segments or as ring segments, for example. As an alternative, however, they may also have any other shape. It is thus possible to obtain information about the dependence of the transmission electrons and the electromagnetic radiation on the angle of incidence.

Moving device 15 of the embodiment presented here is designed in such a way that filter element 13 is movable back and forth relatively between first position A and second position B. For example, filter element 13 may be moved back and forth between first position A and second position B in a very short interval, in particular an interval in the range of 100 ms to 2 s. This makes it possible to perform in particular time-resolved measurements for a preselectable location on object 9.

Figure 2:
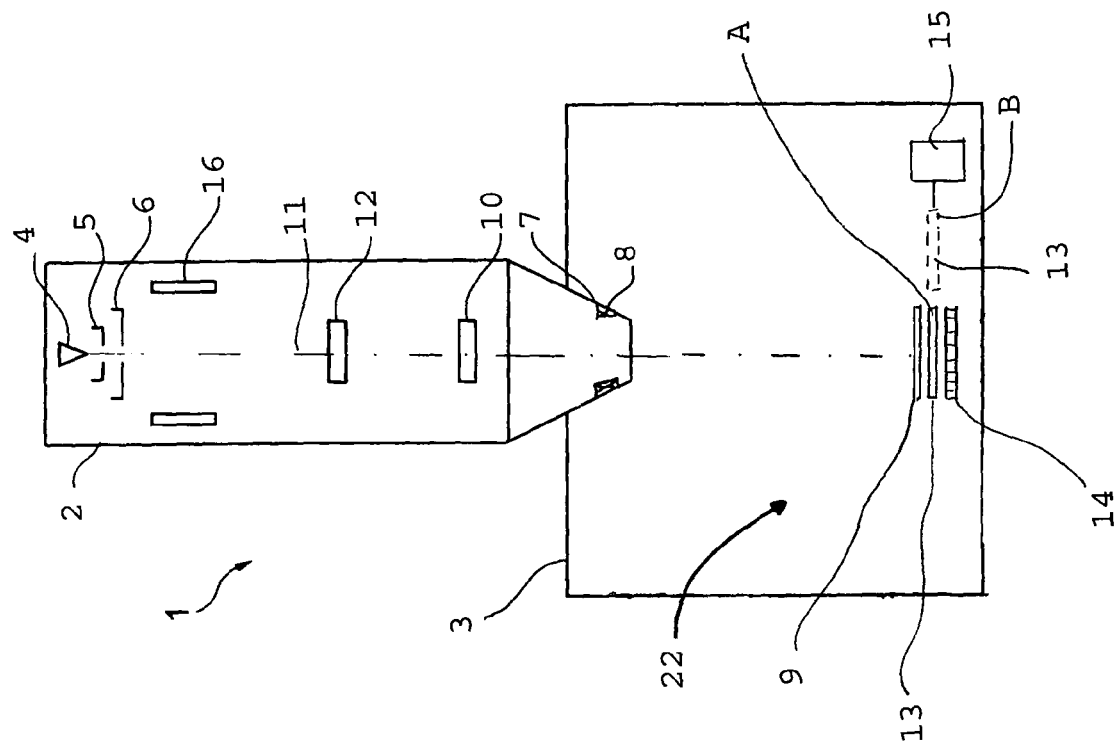
FIG. 2 shows a schematic view of a second exemplary embodiment of a particle beam device according to the system described herein.

FIG. 2 shows a schematic view of a second exemplary embodiment of a particle beam device 1 according to the system described herein. Particle beam device 1 according to FIG. 2 is based on particle beam device 1 according to FIG. 1. The same components are therefore labeled with the same reference numerals. The only difference between particle beam device 1 according to FIG. 2 and particle beam device 1 according to FIG. 1 is the placement of moving device 15, which is situated in sample chamber 3, in particle beam device 1 according to FIG. 2. It is therefore no longer necessary to provide vacuum feed-throughs for moving device 15.

Figure 3:
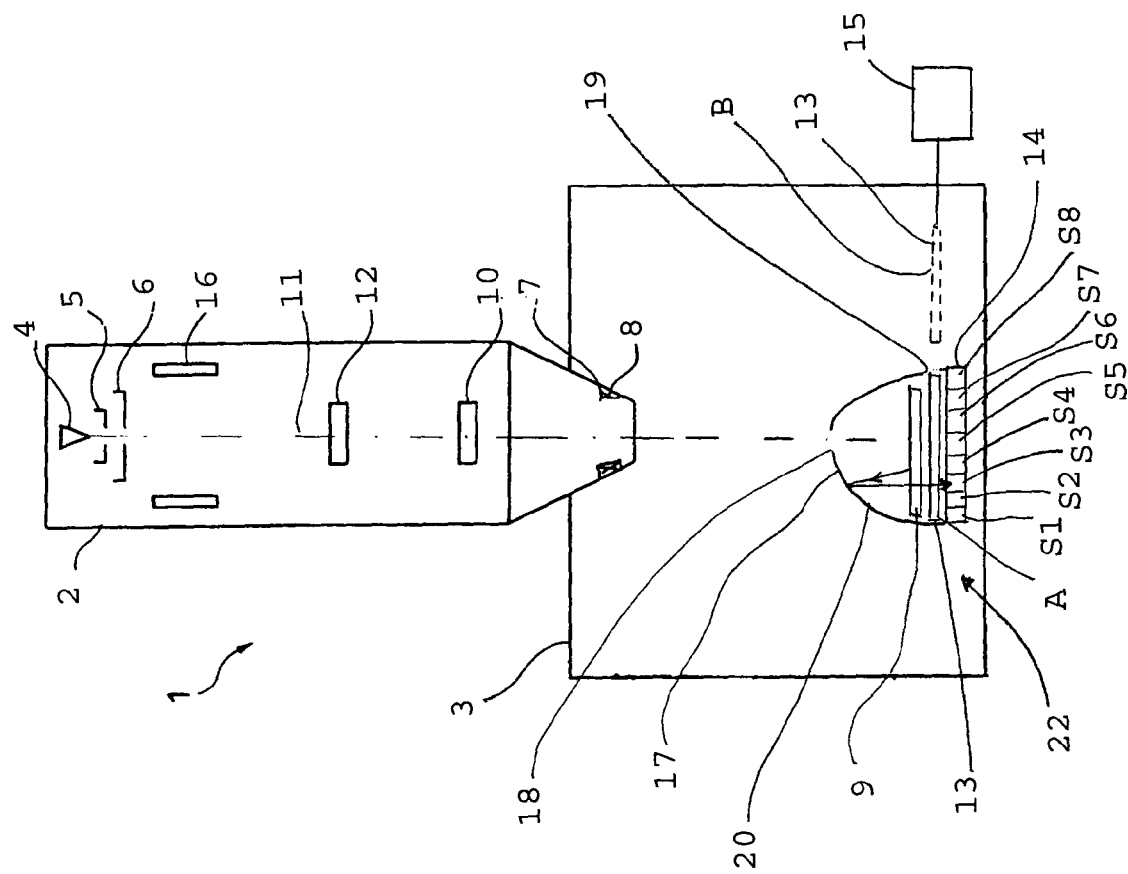
FIG. 3 shows a schematic view of a third exemplary embodiment of a particle beam device according to the system described herein.

FIG. 3 shows a schematic view of a third exemplary embodiment of a particle beam device 1 according to the system described herein. Particle beam device 1 according to FIG. 3 is based on particle beam device 1 according to FIG. 1. The same components are therefore provided with the same reference numerals. Particle beam device 1 according to FIG. 3 additionally has a reflective unit 17 which belongs to the detection device 22 and is designed as a hemisphere having a maximum diameter in the range of 0.3 cm to 30 cm. Reflective unit 17 has a first through opening 18 through which the primary electron beam may pass toward object 9. Furthermore, a second through opening 19 through which filter element 13 may be brought from first position A into second position B (and vice-versa) is provided on reflective unit 17. On its side facing inward, reflective unit 17 has a reflective layer 20 produced by polishing aluminum, for example. However, reference is made explicitly to the fact that the system described herein is not limited to such a reflective layer 20. Instead, any suitable reflective layer 20 suitably manufactured, for example, by sputtering or vapor deposition, may be used.

Reflective unit 17 is situated movably. Reflective unit 17 is movable between a reflection position and a resting position. In the reflection position, reflective unit 17 covers object 9, third detector 14, and filter element 13 if it is in first position A. In the resting position, reflective unit 17 is moved, for example, in a direction perpendicular to optical axis 11 and running into the plane of the page. In the resting position, reflective unit 17 no longer covers object 9 and third detector 14.

Using the reflective unit 17, a portion of the electromagnetic radiation is reflected toward third detector 14. Object 9 of this exemplary embodiment is transparent to the electromagnetic radiation. Object 9 is transparent here to the electromagnetic radiation of a wavelength range in which the wavelength of the electromagnetic radiation emitted by object 9 also occurs. The electromagnetic radiation emitted by object 9 not toward the third director 14 but rather in the direction opposite third detector 14 is reflected on the reflective layer 20, passing through object 9 and through filter element 13 and then striking third detector 14. It is thus possible to detect not only the electromagnetic radiation emitted into the first half-space directed to third detector 14 but also to detect the electromagnetic radiation emitted in the second half-space opposite the first half-space. In this way, detection of the electromagnetic radiation over the total solid angle ($4\pi$ detection) is possible.

In an alternative embodiment (not shown), reflective unit 17 may be designed in such a way that object 9, filter element 13, detector 14 and moving device 15 are covered by reflective unit 17. Thus in this embodiment it is not absolutely necessary for reflective unit 17 to be moved. In the aforementioned embodiment, however, object 9 is designed to be much smaller than detector 14. Furthermore, if object 9, because of its thickness or because of the material of which it is made, is not transparent to electromagnetic radiation, detector 14 is nevertheless able to detect electromagnetic radiation emitted from the surface of object 9 and reflected by reflective unit 17.

Figure 4:
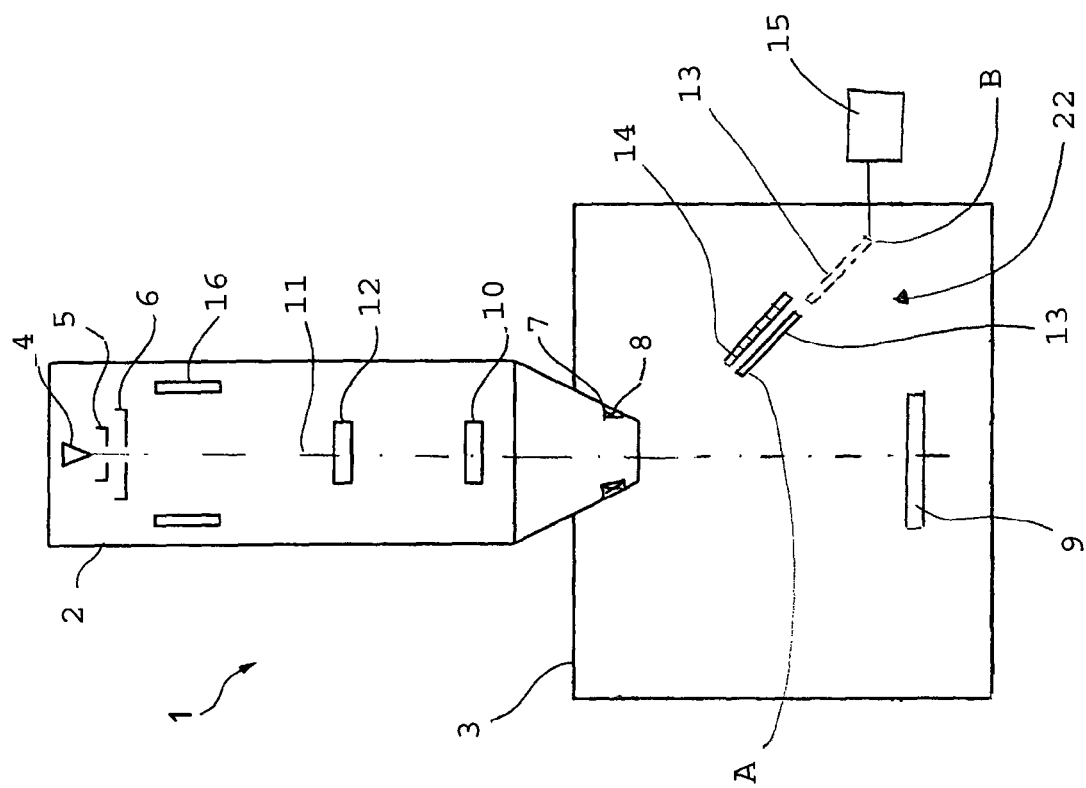
FIG. 4 shows a schematic view of a fourth exemplary embodiment of a particle beam device according to the system described herein.

FIG. 4 shows a schematic view of a fourth exemplary embodiment of a particle beam device 1 according to the system described herein. Particle beam device 1 according to FIG. 4 is based on particle beam device 1 according to FIG. 1. The same components are therefore labeled with the same reference numerals. To this extent, reference is made first to the preceding discussion. Particle beam device 1 according to FIG. 4 differs from particle beam device 1 according to FIG. 1 in that third detector 14 and filter element 13 are situated offset by an angle of approximately 45° to optical axis 11 in an area between object 9 and objective lens 7. Here again, moving device 15 is provided, so that filter element 13 is movable back and forth between first position A and second position B. In the exemplary embodiment shown here, third detector 14 is designed for detecting electromagnetic radiation, secondary electrons and backscattered electrons. Filter element 13 is used to filter the secondary electrons and the backscattered electrons.

Figure 5:
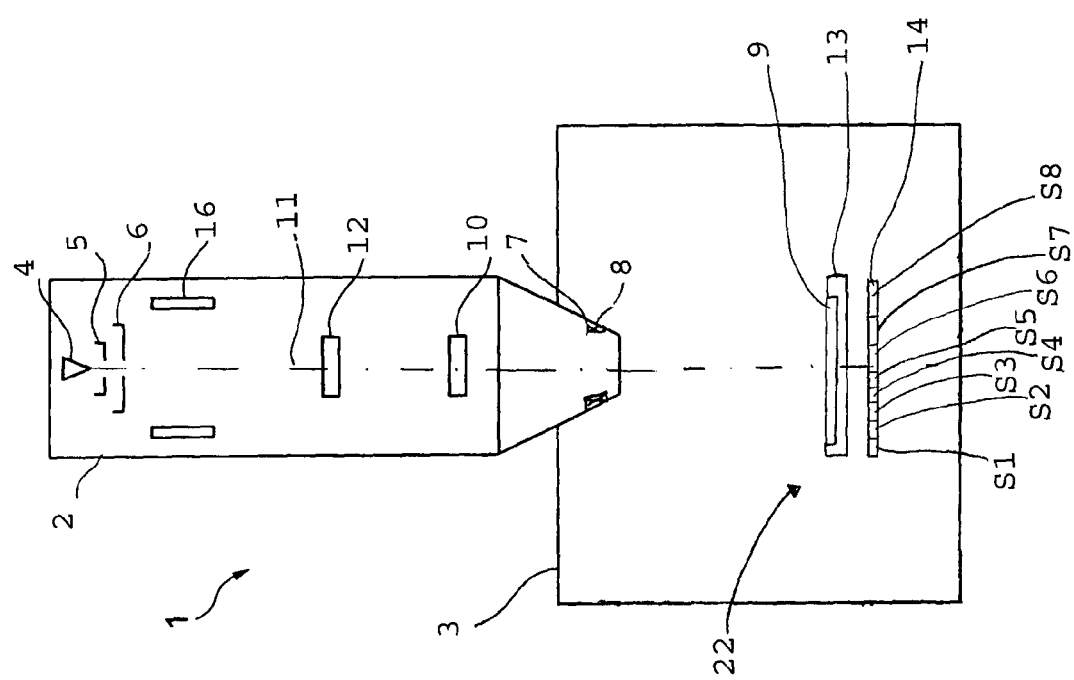
FIG. 5 shows a schematic view of a fifth exemplary embodiment of a particle beam device according to the system described herein

FIG. 5 shows a schematic view of a fifth exemplary embodiment of a particle beam device 1 according to the system described herein. Particle beam device 1 according to FIG. 5 is based on particle beam device 1 according to FIG. 1. The same components are therefore labeled with the same reference numerals. To this extent, reference is made first to the preceding discussion. Particle beam device 1 according to FIG. 5 differs from particle beam device 1 according to FIG. 1 in that filter element 13 is designed as an object holder in which object 9 is embedded. Filter element 13 is in the form of a microscope slide. In contrast with the exemplary embodiment according to FIG. 1, filter element 13 is not designed to be movable. It is used to filter the transmission electrons.

The exemplary embodiments according to FIGS. 1 through 3 may also be designed as variants of the system described herein. In these variants, filter element 13 may filter the electromagnetic radiation instead of the transmission electrons. The interaction particles are thus transmitted through filter element 13. In first position A of filter element 13, the electromagnetic radiation is prevented from striking third detector 14, so that in second position B, filter element 13 is situated in relation to third detector 14 in such a way that filter element 13 allows electromagnetic radiation to strike third detector 14. The exemplary embodiment according to FIG. 4 may also be designed as described above, but with the difference that filter element 13 allows secondary electrons and backscattered electrons to pass through. The exemplary embodiment according to FIG. 5 may also be designed like the variants from FIGS. 1 and 2, but with the difference that filter element 13 is not movable in the exemplary embodiment according to FIG. 5.

Figure 6:
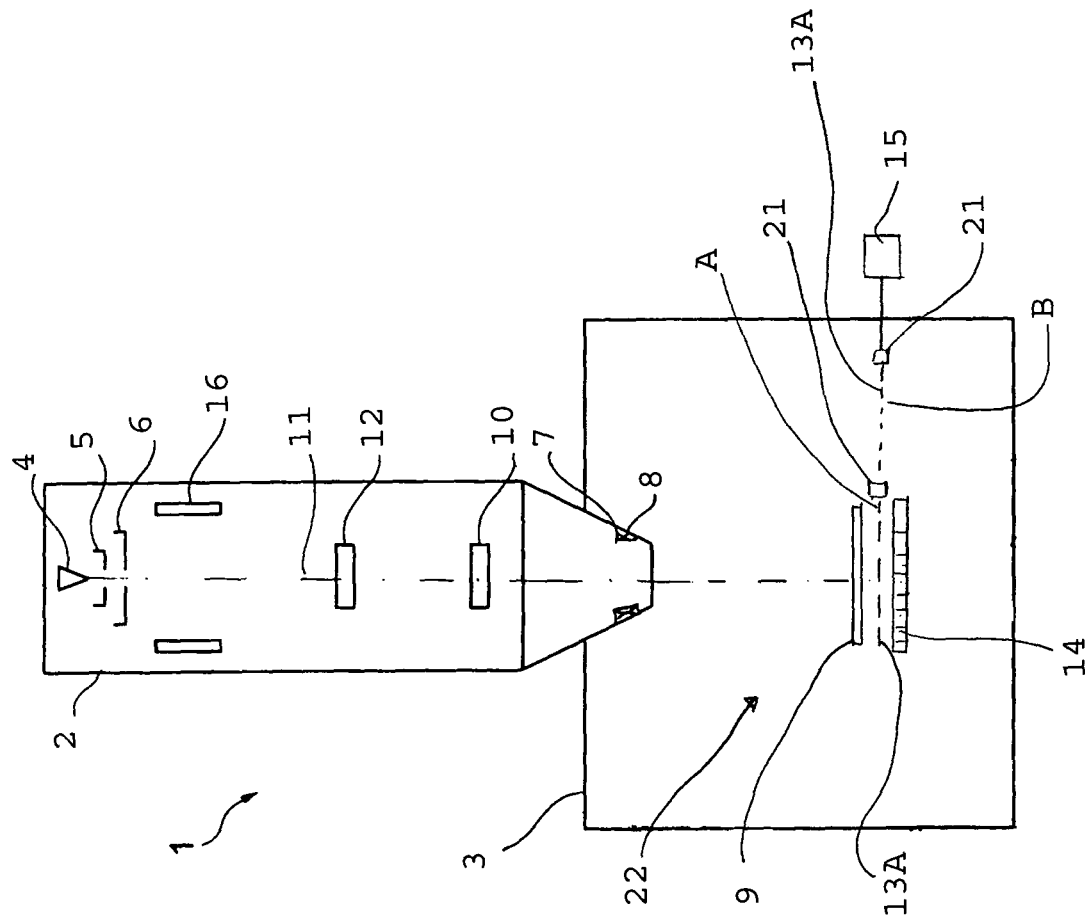
FIG. 6 shows a schematic view of a sixth exemplary embodiment of a particle beam device according to the system described herein.

FIG. 6 shows a schematic view of a sixth exemplary embodiment of a particle beam device 1 according to the system described herein. Particle beam device 1 according to FIG. 6 is based on particle beam device 1 according to FIG. 1. The same components are therefore labeled with the same reference numerals. Therefore, reference is made first to the statements made above. The only difference between particle beam device 1 according to FIG. 6 and particle beam device 1 according to FIG. 1 is the use of an opposing field grid 13A as the filter element, which is situated on a holding device 21 and, by use of moving device 15, is movable from first position A into second position B (and vice-versa). By applying a suitable voltage to opposing field grid 13A, it is possible to deflect transmission electrons in such a way that they do not strike third detector 14. However, the electromagnetic radiation emitted by object 9 does strike third detector 14 and is detected. If opposing field grid 13A is in second position B, then transmission electrons passing through object 9 also strike third detector 14.

The exemplary embodiments shown in the figures may have the effects and advantages already mentioned above, so that reference is made here to this discussion.

Various embodiments discussed herein may be combined with each other in appropriate combinations in connection with the system described herein. Additionally, in some instances, the order of steps in the flowcharts, flow diagrams and/or described flow processing may be modified, where appropriate. Further, various aspects of the system described herein may be implemented using software, hardware, a combination of software and hardware and/or other computer-implemented modules or devices having the described features and performing the described functions. Software implementations of the system described herein may include executable code that is stored in a computer readable storage medium and executed by one or more processors. The computer readable storage medium may include a computer hard drive, ROM, RAM, flash memory, portable computer storage media such as a CD-ROM, a DVD-ROM, a flash drive and/or other drive with, for example, a universal serial bus (USB) interface, and/or any other appropriate tangible storage medium or computer memory on which executable code may be stored and executed by a processor. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A detection device, comprising:
   at least one detector positioned to detect at least one of: electromagnetic radiation and interaction particles, wherein both the electromagnetic radiation and the interaction particles are generated by interaction of a particle beam with an object; and
   at least one filter element through which the electromagnetic radiation is transmitted and which prevents the interaction particles from striking the detector, wherein the filter element is situated movably between a first position and a second position, wherein the filter element is situated in the first position relative to the detector in such a way that the filter element prevents the interaction particles from striking the detector, and wherein the filter element is situated in the second position relative to the detector in such a way that the filter element allows the interaction particles to strike the detector.

2. The detection device as recited in claim 1, wherein the at least one detector detects electromagnetic radiation, wherein the electromagnetic radiation is transmitted through the at least one filter and the interaction particles are not transmitted through the at least one filter, and wherein the filter element includes an object holder.

3. The detection device as recited in claim 1, wherein the filter element is made of a non-luminescent material.

4. The detection device as recited in claim 1, wherein the filter element is made of silicon dioxide.

5. The detection device as recited in claim 1, further comprising:
   a reflective unit which is situated movably between at least one reflection position and at least one resting position, and wherein, in the reflection position, the reflective unit reflects at least a portion of the electromagnetic radiation toward the detector.

6. The detection device as recited in claim 1, wherein the detector includes at least one first detector segment and at least one second detector segment.

7. The detection device as recited in claim 1, further comprising:
   a moving device that moves the filter element, wherein the moving device allows the filter element to move back and forth between the first position and the second position in a predefinable period of time.

8. The detection device as recited in claim 7, wherein the predefinable period of time is in a range from 100 ms to 2 s.

9. The detection device as recited in claim 1, wherein the detector is a semiconductor detector.

10. The detection device as recited in claim 1, wherein the detector has at least one of the following properties: (i) the detector detects luminescence and (ii) the detector is a STEM detector.

11. The detection device as recited in claim 10, wherein the luminescence is at least one of: cathodoluminescence and fluorescence.

12. A particle beam device, comprising:
   a sample chamber;
   an object situated in the sample chamber;
   a beam generator that generates a particle beam;
   an objective lens that focuses the particle beam on the object, wherein, when the particle beam strikes the object, interaction particles and electromagnetic radiation occur due to the interactions of the particle beam with the object; and
   at least one detection device situated in the sample chamber, wherein the at least one detection device includes:
      at least one detector positioned to detect at least one of: electromagnetic radiation and interaction particles, wherein both the electromagnetic radiation and the interaction particles are generated by interaction of the particle beam with the object; and
      at least one filter element through which the electromagnetic radiation is transmitted and which prevents the interaction particles from striking the detector, wherein the filter element is situated movably between a first position and a second position, wherein the filter element is situated in the first position relative to the detector in such a way that the filter element prevents the interaction particles from striking the detector, and wherein the filter element is situated in the second position relative to the detector in such a way that the filter element allows the interaction particles to strike the detector.

13. The particle beam device as recited in claim 12, further comprising at least one of:
   (i) a reflective unit that is situated movably between at least one reflection position and at least one resting position, and wherein, in the reflection position, the reflective unit reflects a portion of the electromagnetic radiation toward the detector; and
   (ii) a moving device that moves the filter element, wherein the moving device moves the filter element between the first position and the second position in a predefinable period of time.

14. The particle beam device as recited in claim 13, wherein at least one of: the reflective unit and the moving device is situated in the sample chamber.

15. The particle beam device as recited in claim 12, wherein the particle beam device further comprises:
   an optical axis, wherein first the object and then the detector are situated along the optical axis, starting from the beam generator toward the object.

16. A method of using a detection device to examine an object, comprising:
   disposing the object for examination by the detection device; and detecting luminescence of the object using the detection device, wherein the luminescence is detected in a predefinable solid angle in the examination, and wherein the detection device includes:
      at least one detector positioned to detect at least one of: electromagnetic radiation and interaction particles, wherein both the electromagnetic radiation and the interaction particles are generated by interaction of a particle beam with the object; and
      at least one filter element through which the electromagnetic radiation is transmitted and which prevents the interaction particles from striking the detector, wherein the filter element is situated movably between a first position and a second position, wherein the filter element is situated in the first position relative to the detector in such a way that the filter element prevents the interaction particles from striking the detector, and wherein the filter element is situated in the second position relative to the detector in such a way that the filter element allows the interaction particles to strike the detector.

17. The method as recited in claim 16, wherein the predefinable solid angle is less than or equal to $4\pi$.

18. The method as recited in claim 16, wherein the object is a biological sample and wherein the luminescence includes at least one of: cathodoluminescence and fluorescence.

19. The method as recited in claim 16, further comprising at least one of:
   (i) moving a reflective unit between at least one reflection position and at least one resting position, and wherein, in the reflection position, the reflective unit reflects a portion of the electromagnetic radiation toward the detector, and
   (ii) moving the filter element using a moving device, wherein the moving device moves the filter element between the first position and the second position in a predefinable period of time.

20. The method as recited in claim 16, wherein the object is a transparent object.

21. A detection device, comprising:
   at least one detector positioned to detect at least one of: electromagnetic radiation and interaction particles, wherein the electromagnetic radiation and the interaction particles are generated by interaction of a particle beam with an object; and
   at least one filter element through which the electromagnetic radiation is transmitted and through which the interaction particles are not transmitted, wherein the filter element includes an object holder.

22. A detection device, comprising:
   at least one detector positioned to detect at least one of: electromagnetic radiation and interaction particles, wherein both the electromagnetic radiation and the interaction particles are generated by interaction of a particle beam with an object; and
   at least one filter element through which the interaction particles are transmitted and which prevents the electromagnetic radiation from striking the detector, wherein the filter element is situated movably between a first position and a second position, wherein the filter element is situated in the first position relative to the detector in such a way that the filter element prevents the electromagnetic radiation from striking the detector, and wherein the filter element is situated in the second position relative to the detector in such a way that the filter element allows the electromagnetic radiation to strike the detector.

* * * * *